United States Patent
Glick et al.

(10) Patent No.: US 7,910,714 B2
(45) Date of Patent: *Mar. 22, 2011

(54) MONOMERIC RED FLUORESCENT PROTEINS

(75) Inventors: Benjamin S. Glick, Chicago, IL (US);
Brooke Bevis, Somerville, MA (US);
Daniel E. Strongin, Chicago, IL (US);
David Baker, Seattle, WA (US);
Michelle Scalley-Kim, Seattle, WA (US)

(73) Assignees: The University of Chicago, Chicago, IL (US); The University of Washington, Seattle, WA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/689,276

(22) Filed: Jan. 19, 2010

(65) Prior Publication Data

US 2010/0184954 A1 Jul. 22, 2010

Related U.S. Application Data

(63) Continuation of application No. 11/748,641, filed on May 15, 2007, now Pat. No. 7,671,185, which is a continuation of application No. 11/100,988, filed on Apr. 7, 2005, now Pat. No. 7,250,298.

(60) Provisional application No. 60/560,340, filed on Apr. 7, 2004.

(51) Int. Cl.
*C07H 21/04* (2006.01)
*A61K 38/00* (2006.01)

(52) U.S. Cl. .................... 536/23.1; 435/440; 435/172.1; 530/350

(58) Field of Classification Search .................... None
See application file for complete search history.

(56) References Cited

U.S. PATENT DOCUMENTS

| | | |
|---|---|---|
| 972,638 A | 10/1910 | Pease et al. |
| 4,302,536 A | 11/1981 | Longenecker |
| RE30,985 E | 6/1982 | Cartaya |
| 4,399,216 A | 8/1983 | Axel et al. |
| 4,551,433 A | 11/1985 | DeBoer |
| 4,560,655 A | 12/1985 | Baker |
| 4,657,866 A | 4/1987 | Kumar |
| 4,683,195 A | 7/1987 | Mullis et al. |
| 4,683,202 A | 7/1987 | Mullis |
| 4,745,051 A | 5/1988 | Smith et al. |
| 4,767,704 A | 8/1988 | Cleveland et al. |
| 4,837,148 A | 6/1989 | Cregg |
| 4,927,762 A | 5/1990 | Darfler |
| 4,929,555 A | 5/1990 | Cregg et al. |
| 5,182,202 A | 1/1993 | Kajiyama et al. |
| 5,221,623 A | 6/1993 | Legocki et al. |
| 5,229,285 A | 7/1993 | Kajiyama et al. |
| 5,330,906 A | 7/1994 | Kajiyama et al. |
| 5,418,155 A | 5/1995 | Cormier et al. |
| 5,439,797 A | 8/1995 | Tsien et al. |
| 5,484,956 A | 1/1996 | Lundquist et al. |
| 5,491,084 A | 2/1996 | Chalfie et al. |
| 5,538,879 A | 7/1996 | Muller-Rober et al. |
| 5,576,198 A | 11/1996 | McBride et al. |
| 5,595,896 A | 1/1997 | Coruzzi et al. |
| 5,618,722 A | 4/1997 | Zenno et al. |
| 5,629,470 A | 5/1997 | Lam et al. |
| 5,633,155 A | 5/1997 | Kim et al. |
| 5,641,670 A | 6/1997 | Treco et al. |
| 5,650,135 A | 7/1997 | Contag et al. |
| 5,654,173 A | 8/1997 | Jacobs et al. |
| 5,656,466 A | 8/1997 | Moon et al. |
| 5,674,713 A | 10/1997 | McElroy et al. |
| 5,674,731 A | 10/1997 | Lin et al. |
| 5,688,648 A | 11/1997 | Mathies et al. |
| 5,689,045 A | 11/1997 | Logemann et al. |
| 5,689,049 A | 11/1997 | Cigan et al. |
| 5,700,673 A | 12/1997 | McElroy et al. |
| 5,707,804 A | 1/1998 | Mathies et al. |
| 5,728,528 A | 3/1998 | Mathies et al. |
| 5,733,761 A | 3/1998 | Treco et al. |
| 5,739,409 A | 4/1998 | Fischer et al. |
| 5,750,870 A | 5/1998 | Mathews et al. |
| 5,767,367 A | 6/1998 | Dudits et al. |
| 5,795,737 A | 8/1998 | Seed et al. |
| 5,804,387 A | 9/1998 | Cormack et al. |
| 5,824,485 A | 10/1998 | Thompson et al. |
| 5,843,746 A | 12/1998 | Tatsumi et al. |
| 5,863,727 A | 1/1999 | Lee et al. |
| 5,866,336 A | 2/1999 | Nazarenko et al. |
| 5,869,255 A | 2/1999 | Mathies et al. |
| 5,874,304 A | 2/1999 | Zolotukhin et al. |
| 5,911,952 A | 6/1999 | Tsuji |
| 5,919,445 A | 7/1999 | Chao |
| 5,945,283 A | 8/1999 | Kwok et al. |
| 5,945,526 A | 8/1999 | Lee et al. |

(Continued)

FOREIGN PATENT DOCUMENTS

DE 19718640 A 7/1999

(Continued)

OTHER PUBLICATIONS

Altschul, S.F. et al., "Basic local alignment search tool," *J. Mol. Biol.* (1990) 215:403-410.

Anderluh, G. et al., "Cloning, Sequencing, and Expression of Equinatoxin II," *Biochem. Biophys. Res. Comm.* (1996) 220:437-442.

Animal Cell Culture, a practical approach, R.I. Freshney, ed., IRL Press, Oxford-Washington DC, (1986) (Book Not Provided/Table of Contents Only).

Atwell et al., "Structural Plasticity in a Remodeled Protein-Protein Interface," *Science* (1997) 278:1125-1128.

Baird, G.S. et al., "Biochemistry, mutagenesis, and oligomerization of DsRed, a red fluorescent protein from coral," Proc. Natl. Acad. Sci. USA (2000) 97:11984-11989.

(Continued)

*Primary Examiner* — Anand U Desai
*Assistant Examiner* — Samuel Liu
(74) *Attorney, Agent, or Firm* — Andrus, Sceales, Starke & Sawall, LLP

(57) ABSTRACT

Disclosed are sequences encoding monomeric variants of DsRed fluorescent proteins and methods of use.

4 Claims, 2 Drawing Sheets

U.S. PATENT DOCUMENTS

| | | | |
|---|---|---|---|
| 5,958,713 | A | 9/1999 | Thastrup et al. |
| 5,968,738 | A | 10/1999 | Anderson et al. |
| 5,968,750 | A | 10/1999 | Zolotukhin et al. |
| 5,976,796 | A | 11/1999 | Szalay et al. |
| 5,981,200 | A | 11/1999 | Tsien et al. |
| 5,985,577 | A | 11/1999 | Bulinski |
| 5,989,835 | A | 11/1999 | Dunlay et al. |
| 5,998,146 | A | 12/1999 | Latva et al. |
| 6,008,373 | A | 12/1999 | Waggoner et al. |
| 6,020,192 | A | 2/2000 | Muzyczka et al. |
| 6,066,476 | A | 5/2000 | Tsien et al. |
| 6,130,313 | A | 10/2000 | Li et al. |
| 6,306,600 | B1 | 10/2001 | Kain et al. |
| 7,005,511 | B2 | 2/2006 | Tsien et al. |
| 7,250,298 | B2 | 7/2007 | Glick et al. |
| 7,671,185 | B2 | 3/2010 | Glick et al. |
| 2002/0197676 | A1 | 12/2002 | Lukyanov et al. |
| 2003/0059835 | A1 | 3/2003 | Tsien et al. |
| 2003/0170911 | A1 | 9/2003 | Tsien et al. |
| 2005/0149994 | A1 | 7/2005 | Bevis et al. |
| 2006/0275827 | A1 | 12/2006 | Campbell et al. |

FOREIGN PATENT DOCUMENTS

| | | |
|---|---|---|
| EP | 0036776 | 9/1981 |
| EP | 0155476 | 9/1985 |
| EP | 0127839 | 7/1992 |
| EP | 0244234 | 7/1993 |
| WO | WO 87/00195 | 1/1987 |
| WO | WO 90/03430 | 4/1990 |
| WO | WO 90/04036 | 4/1990 |
| WO | WO 90/10077 | 9/1990 |
| WO | WO 91/00357 | 1/1991 |
| WO | WO 92/02190 | 2/1992 |
| WO | WO 99/15650 | 4/1999 |
| WO | WO 99/49019 | 9/1999 |
| WO | WO 00/02997 | 1/2000 |
| WO | WO 00/03246 | 1/2000 |
| WO | WO 00/17624 | 3/2000 |
| WO | WO 00/17643 | 3/2000 |
| WO | WO 00/26408 | 5/2000 |
| WO | WO 00/46233 | 8/2000 |
| WO | WO 01/27150 | 4/2001 |
| WO | WO 02/40539 | 5/2002 |
| WO | WO 02/068459 | 9/2002 |
| WO | WO 03/054158 | 7/2003 |
| WO | WO 2005/100387 | 10/2005 |
| WO | WO 2009/059305 | 5/2009 |

OTHER PUBLICATIONS

Ballance, D.J. et al., "Transformation of *Aspergillus nidulans* by the orotidine-5'-phosphate decarboxylase gene of *Neurospora crassa*," Biochem. Biophys. Res. Commun. (1983) 112(1):284-289.

Barton, M.C. et al., "Site-directed, recombination-mediated mutagenesis of a complex gene locus," Nucleic Acids Res. (1990) 18(24):7349-7355.

Beach, D. et al., "Functionally homologous cell cycle control genes in budding and fission yeast," Nature (1982+B22) 300:706-709.

Beernink, P.T. et al., "Disruption of the aldolase A tetramer into catalytically active monomers," Proc. Natl. Acad. Sci. USA (1996) 93:5374-5379.

Bevis, B.J.et al., "Rapidly maturing variants of the Discosoma red fluorescent protein (DsRed)," Nat. Biotechnol. (2002) 20:83-87.

Bogan, A.A. and Thorn, K.S., "Anatomy of hot spots in protein interfaces," J. Mol. Biol. (1998) 280:1-9.

Boshart, M. et al., "A very strong enhancer is located upstream of an immediate early gene of human cytomegalovirus," Cell (1985) 41:521-530.

Cadwell, R.C. and Joyce, G.F., "Mutagenic PCR," PCR Primer:B27 A Laboratory Manual (1995) Dieffenbach and Dveksler, eds., Cold Spring Harbor Laboratory Press, 583-589.

Campbell, R.E. et al., "A monomeric red fluorescent protein," Proc. Natl. Acad. Sci. USA (2002) 99(12):7877-7882.

Carbonell, L.F. et al., "Synthesis of a gene coding for an insect-specific scorpion neurotoxin and attempts to express it using baculovirus vectors," Gene (1988) 73:409-418.

Colicelli, J. et al., "A temperature-sensitive mutation constructed by 'linker insertion' mutagenesis," Mol. Gen. Genet. (1985) 199:537-539.

Condeelis, J.S. et al., "Imaging of Cancer Invasion and Metastasis Using Green Fluorescent Protein," Eur. J. Cancer (2000) 36:1671-1680.

Cormack, B.P. et al., "FACS-optimized Mutants of the Green Fluorescent Protein (GFP)," Gene (1996) 173:33-38.

Cregg, J.M. et al., "*Pichia pastoris* as a host system for transformations," Mol. Cell Biol. (1985) 5(12):3376-3385.

Cronin et al., "A Genetics-Friendly GFP Assay," Trends Cell Biol. (1999) 9:36.

Cubitt, A.B. et al., "Understanding Structure-Function Relationships in the *Aequoria victoria* Green Fluorescent Protein," *Methods in Cell Biology* (1999) 58:19-30.

Das, S. et al., "Transformation of *Kluyveromyces fragilis*," J. Bacteriol. (1984) 158(3):1165-1167.

Davidow, L.S. et al., "Integrative transformation of the yeast *Yarrowia lipolytica*," Curr. Genet. (1985) 10:39-48.

De Boer, H.A. et al., "The *tac* promoter: A functional hybrid derived from the *trp* and *lac* promoters," Proc. Natl. Acad. Sci. USA (1983) 80:21-25.

De Giorgi, F. et al., "Targeting GFP to organelles," *Methods in Cell Biology* (1999), Sullivan and Kay, eds., Academic Press, San Diego, 58:75-85.

De Louvencourt, L. et al., "Transformation of *Kluyveromyces lactis* by killer plasmid DNA," J. Bacteriol. (1983) 154(2):737-742.

Demeler, B. et al., "Determination of Molecular Parameters by Fitting Sedimentation Data to Finite-Element Solutions of the Lamm Equation," Biophys. J. (1998) 74:444-454.

Deo et al., "Luminescent Proteins from *Aequorea victoria*: Applications in Drug Discovery and in High Throughput Analysis," Fresenius J. Anal. Chem. (2001) 369:258-266.

Dickson, R.M. et al., "On/off Blinking and Switching Behavior of Single Molecules of Green Fluorescent Protein," Nature (1997) 388:355-358.

Dijkema, R. et al., "Cloning and expression of the chromosomal immune interferon gene of the rat," EMBO J. (1985) 4(3):761-767.

Dittrich, P. et al., "Accessing molecular dynamics in cells by fluorescence correlation spectroscopy," Biol. Chem. (2001) 382:491-494.

DNA Cloning: A Practical Approach, vols. I and II (D.N. Glover ed), IRL Press Oxford-Washington DC (1985) (Book Not Provided/Table of Contents Only).

Dove, S.G. et al., "Isolation and partial characterization of the pink and blue pigments of pocilloporid and acroporid corals," Biol. Bull. (1995) 189:288-297.

Dunn, A.K. et al., "New rfp- and pES213-derived tools for analyzing symbiotic *Vibrio fischeri* reveal patterns of infection and lux expression in situ," Appl. Environ. Microbiol. (2006) 72(1):802-810.

Ellenberg, J. et al., "Dual-color imaging with GFP variants," Trends Cell Biol.(1999) 9:52-56.

Fischer et al., "A Brilliant Monomeric Red Fluorescent Protein to Visualize Cytoskeleton Dynamics in *Dictyostelium*," FEBS Letters (2004) 577:277-232.

Fradkov, A.F. et al., "Novel fluorescent protein from *Discosoma* coral and its mutants possesses a unique far-red fluorescence," FEBS Lett. (2000) 479:127-130.

Friesen, P.D. et al., "The regulation of baculovirus gene expression," *Current Topics in Microbiology and Immunology*, (1986) 131:31-49.

Garcia-Parajo, M.F. et al., "The Nature of Fluorescence Emission in the Red Fluorescent Protein DsRed, Revealed by Single-molecule Detection," Proc. Natl. Acad. Sci. USA (2001) 98:14392-14397.

Garcia-Parajo, M.F. et al., "Visualizing individual green fluorescent proteins with a near field optical microscope," Cytometry (1999) 36:239-246.

Gleeson, M.A. et al., "Transformation of the methylotrophic yeast *Hansenula polymorpha*," Gen. Microbiol. (1986) 132:3459-3465.

Goeddel, D.V. et al., "Direct expression in *Escherichia coli* of a DNA sequence coding for human growth hormone," Nature (1979) 281:544-548.

Goeddel, D.V. et al., "Synthesis of human fibroblast interferon by *E. coli*," Nucleic Acids Res. (1980) 8:18:4057-4073.

Gorman, C.M. et al., "The Rous sarcoma virus long terminal repeat is a strong promoter when introduced into a variety of eukaryotic cells by DNA-mediated transfection," Proc. Natl. Acad. Sci. USA (1982) 79:6777-6781.

Gross, L.A. et al., "The structure of the chromophore within DsRed, a red fluorescent protein from coral," Proc. Natl. Acad. Sci. USA (2000) 97:22:11990-11995.

Grosschedl, R. and Baltimore, D., "Cell-type specificity of immunoglobulin gene expression is regulated by at least three DNA sequence elements," Cell (1985) 41:885-897.

Guide to Protein Purification, Deutscher, ed., Academic Press (1990) (Book Not Provided/Table of Contents Only).

Gurskaya, N.G. et al., "Color transitions in coral's fluorescent proteins by site-directed mutagenesis," BMC Biochem. (2001) 2:6.

Gurskaya, N.G. et al., "GFP-like chromoproteins as a source of far-red fluorescent proteins," FEBS Lett. (2001) 507:16-20.

Gustin, K.E. and Burk, R.D., "A rapid method for generating linker scanning mutants utilizing PCR," Biotechniques (1993) 14:1:22-23.

Harms, G.S. et al., "Autofluorescent proteins in single-molecule research: applications to live cell imaging microscopy," Biophys. J. (2001) 80:2396-2408.

Harvey, E.N., Bioluminescence, New York, Academic Press (1952) (Book Not Provided/Table of Contents Only).

Hastings, J.W., "Bioluminescence," Cell Physiology (1995), N. Speralakis, ed, New York, Academic Press, 665-681.

Haugwitz, M. et al., "Characterization of the improved red fluorescent protein DsRed2," Soc. for Neuroscience Abstracts(2001) 27(1):351.

Hawley, T.S. et al., "Four-color flow cytometric detection of retrovirally expressed red, yellow, green, and cyan fluorescent proteins," BioTechniques (2001) 30:1028-1034.

Heikal, A.A. et al., "Molecular spectroscopy and dynamics of intrinsically fluorescent proteins: coral red (dsRed) and yellow (Citrine)," Proc. Natl. Acad. Sci. (2000) 97(22):11986-12001.

Heim, R. et al., "Improved green fluorescence," Nature (1995) 373:663-664.

Heim, R. and Tsien, R.Y., "Engineering green fluorescent protein for improved brightness, longer wavelengths and fluorescent resonance energy transfer," Curr. Biol. (1996) 6:2:178-182.

Ju, G. et al., "Conversion of the interleukin 1 receptor antagonist into an agonist by site-specific mutagenesis," Proc. Natl. Acad. Sci USA (1991) 88:2658-2662.

Kilgard et al., "Anticipated Stimuli Across Skin," Nature 373:663, (1995).

Higgins, D.G. and Sharp, P.M., "Fast and sensitive multiple sequence alignments on a microcomputer," CABIOS Comm. (1989) 5(2):151-153.

Hinnen, A. et al., "Transformation of yeast," Proc. Natl. Acad. Sci. USA (1978) 75(4):1929-1933.

Hu, J.C., "Repressor fusions as a tool to study protein-protein interactions," Structure (1995) 3:5:B77431-433.

Immobilised Cells and Enzymes, a Practical Approach, J. Woodward, ed., IRL Press, Oxford-Washington DC (1986) (Book Not Provided/Table of Contents Only).

Ito, H. et al., "Transformation of intact yeast cells treated with alkali cations," J. Bacteriol. (1983) 153(1):163-168.

"IUPAC-IUB commission on biochemical nomenclature a one-letter notation for amino acid sequences tentative rules," J. Biol. Chem. (1968) 243(13):3557-3559.

Jakobs, S. et al., "EGFP and DsRed Expressing Cultures of Escherichia coli Imaged by Confocal, Two-Photon and Fluorescence Lifetime Microscopy," FEBS Lett. (2000) 479:131-135.

Jones, D.H. and Winistorfer, S.C., "Recombinant circle PCR and recombination PCR for site-specific mutagenesis without PCR product purification," Biotechniques (1992) 12(4):528-533.

Jost, C.R. et al., "Mammalian expression and secretion of functional single-chain Fv molecules," J. Biol. Chem. (1994) 269(42):26267-26273.

Kabat, E.A. et al., Sequences of Proteins of Immunological Interest (1991) NIH publication No. 91-3242 (Book Not Provided/Table of Contents Only).

Kelly, J.M. and Hynes, M.J., "Transformation of Aspergillus niger by the amdS gene of Aspergillus nidulans," EMBO J. (1985) 4(2):475-479.

Klasen, M. et al., "Silent point mutation in DsRed resulting in enhanced relative fluorescence intensity," Biotechniques (2004) 36(2):236-238.

Klebanoff, S. et al., "Metabolic similarities between fertilization and phagocytosis. Conservation of peroxidatic mechanism," J. Exp. Med. (1979) 149:938-953.

Knop et al., "Improved Version of the Red Fluorescent Protein (drFP583/DSRed/RFP)," BioTechniques (2002) 33:3:592,594,596-598,600,602.

Kubitscheck, U. et al., "Imaging and Tracking of Single GFP Molecules in Solution," Biophys. J. (2000) 78:2170-2179.

Kunze, G. et al., "Transformation of the industrially important yeast Candida maltosa and Pichia guilliermondii," J. Basic Microbiol. (1985) 25:2:141-144.

Kurtz, M.B. et al., "Integrative transformation of Candida albicans, using a cloned Candida ADE2 gene," Mol. Cell Biol, (1986) 6:1:142-149.

Laitinen, O.H. et al., "Biotin Induces Tetramerization of a Recombinant Monomeric Avidin. A Model for Protein-Protein Interactions," J. Biol. Chem. (2001) 276:B928219-8224.

Lakowicz, J.R., Principles of Fluorescence Spectroscopy, 2nd Ed., Kluwer Academic/Plenum Publishers, New York (1999) (Book Not Provided/Table of Contents Only).

Laue et al., "Modern Applications of Analytical Ultracentrifugation," Annu. Rev. Biophys. Biomol. Struct. (1999) 28:75-100.

Lauf, U. et al., "Expression of Fluorescently Tagged Connexins: a Novel Approach to Rescue Function of Oligomeric DsRed-tagged Proteins," FEBS Lett. (2001) 498-11-15.

Lee et al., "Novel Approaches to Monitor Bacterial Gene Expression in Infected Tissue and Host," Curr. Opin. Microbiol. 2000 3:97-101.

Liu, A.Y. et al., "Chimeric mouse-human IgG1 antibody that can mediate lysis of cancer cells," Proc. Natl. Acad. Sci. USA 1987 84:3439-3443.

Liu, A.Y. et al., "Production of a mouse-human chimeric monoclonal antibody to CD20 with potent Fc-dependent biologic activity," J. Immunol. (1987) 139(10):3521-3526.

Luckow, V.A. and Summers, M.D., "Trends in the development of baculovirus expression vectors," Bio/Technology (1988) 6:47-55.

Lukyanov, K. et al., "Natural animal coloration can be determined by a nonfluorescent green fluorescent protein homolog," J. Biol. Chem. (2000) 275(34):25879-25882.

Macek, P. et al., "Intrinsic tryptophan fluorescence of equinatoxin II, a pore-forming polypeptide from the sea anemone Actinia equina L, monitors its interaction with lipid membranes," Eur. J. Biochem. (1995) 234:329-335.

Maeda, S. et al., "Production of human α-interferon in silkworm using a baculovirus vector," Nature (1985) 315:592-594.

Maniatis, T. et al., Molecular Cloning: A Laboratory Manual, Cold Spring Harbor of Laboratory (1982) (Book Not Provided/Table of Contents Only).

Marotti, K.R. and Tomich, C-S.C., "Simple and efficient oligonucleotide-directed mutagenesis using one primer and circular plasmid DNA template," Gene Anal. Tech. (1989) 6:67-70.

Martin, B.M. et al., "Glycosylation and processing of high levels of active human glucocerebrosidase in invertebrate cells using a baculovirus expression vector," DNA (1988) 7(2):99-106.

Martynov, V.I. et al., "Alternative cyclization in GFP-like proteins family," J. Biol. Chem. (2001) 276:24:B12521012-21016.

Matz, M.V. et al., "Fluorescent proteins from nonbioluminescent Anthozoa species," Nat. Biotechnol. (1999) 17:969-973.

McNew, J.A. et al., "Goslp, a Saccharomyces cerevisiae SNARE Protein Involved in Golgi Transport," FEBS Lett. (1998) 435:89-95.

McTigue, M.A. et al., "Crystal Sstructures of a Schistosomal Drug and Vaccine Target: Flutathione S-transferase from Schistosoma japonica and its Complex with the Leading Antischistosomal Praziquantel," J. Mol. Biol. (1995) 246:21-27.

Miller, D.W. et al., "An insect baculovirus host-vector system for high-level expression of foreign genes," Genetic Engineering (1986) 8:277-298.

Miyajima, A. et al., "Use of the silkworm, *Bombyx mori*, and an insect baculovirus vector for high-level expression and secretion of biologically active mouse interleukin-3," Gene (1987) 58:273-281.

Miyawaki, A. et al., "Fluorescent Indicators for Ca2+ Based on Green Fluorescent Proteins and Calmodulin," Nature (1997) 388:882-887.

Mizuno, H. et al., "Red fluorescent protein from *Discosoma* as a fusion tag and a partner for fluorescence resonance energy transfer," Biochem. (2001) 40:2502-2510.

Moerner, W.E. et al., "Optical Methods for Xxploring Dynamics of Single Copies of Green Fluorescent Protein," Cytometry (1999) 36:232-238.

Nucleic Acid Hybridization, a Practical Approach, B.D. Harnes & S.J. Higgins eds., IRL Press, Oxford-Washington DC (1985) (Book Not Provided/Table of Contents Only).

Okayama H. and Berg. P., "A cDNA cloning vector that permits expression of cDNA inserts in mammalian cells," Mol. Cell Biol. (1983) 3(2):280-289.

Oligonucleotide Synthesis, a Practical Approach, M.J. Gait, ed., IRL Press, Oxford-Washington DC (1984) (Book Not Provided/Table of Contents Only).

Pakula, A.A. et al., "Genetic analysis of protein stability and function," Annu. Rev. Genet. (1989) 23:289-310.

Perbal, B., A Practical Guide to Molecular Cloning, John Wiley & Sons, New York (1984) (Book Not Provided/Table of Contents Only).

Pfleger, B.F. et al., "Optimization of DsRed production in *Escherichia coli*; effect of ribosome binding site sequestration on translation efficiency," Biotech. Bioeng. (2005) 92(5):553-558.

Phillips et al., "Structure and Dynamics of Green Fluorescent Protein," Curr. Opin. Struc. Biol. (1997) 7:821-827.

Pierce, D.W. and Vale, R.D., "Single-molecule fluorescence detection of green fluorescence protein and application to single-protein dynamics," *Methods in Cell Biology* (1999) Sullivan and Kay, eds., Academic Press, San Diego 5.

Piston, D.W., "Imaging Living Cells and Tissues by Two-Photon Excitation Microscopy," Trends Cell Biol. (1999) 9:66-69.

Plant Biochemistry and Molecular Biology, Lea & Leegood, eds., John Wiley & Sons (1993) 275-295.

Pokkuluri et al, "A Domain Flip as a Result of a Single Amino-Acid Substitution," Structure (1998) 6:8:1067-1073.

Pollok et al, "Using GFP in FRET-based Applications," Trends Cell Biol. (1999) 9:57-60.

Prentki, P. and Krisch, H.M., "In vitro insertional mutagenesis with a selectable DNA fragment," Gene (1984) 29:303-313.

Radotic, K. et al., "Spontaneous ultraweak bioluminescence in plants: origins, mechanisms and properties," Gen. Physiol. Biophys. (1998) 17:289-308.

Raffen et al., "Small Zone High-Speed Gel Filtration Chromatography to Detect Protein Aggregation Associated with Light Chain Pathologies," Methods Enzymol. (1999) 309:318-332.

Remington, S.J., "Negotiating the Speed Bumps to Fluorescence," Nat. Biotechnol. (2002) 20:28-29.

Roggenkamp, R. et al., "Transformation of the methylotrophic yeast *Hansenula polymorpha* by autonomous replication and integration vectors," *Mol. Gen. Genet.* (1986) 202:302-308.

Rossanese, O.W. et al., "Golgi structure correlates with transitional endoplasmic reticulum organization in *Pichia pastoris* and *Saccharomyces cerevisiae*," *J. Cell Biol.* (1999) 145(1):69-81.

Rossanese et al., "A Role for Actin, Cdc1p and Myo2p in the Inheritance of Late Golgi Elements in *Saccharomyces cerevisiae*," J. Cell Biol. (2001) 153:47-61.

Sambrook, J. et al., Molecular Cloning: A Laboratory Manual, 2nd Ed. (1989) Cold Spring Harbor Press, Cold Spring Harbor, New York, 15.3-15.108.

Sayers, J.R. et al., "Rapid high-efficiency site-directed mutagenesis by the phosphorothioate approach," *BioTechniques* (1992) 13(4):592-596.

Schomer, B. and Epel, D., "Redox changes during fertilization and maturation of marine invertebrate eggs," Dev. Biol. (1998) 203:1-11.

Schwille, P. et al., "Molecular dynamics in living cells observed by fluorescence correlation spectroscopy with one- and two-photon excitation," Biophys. J. (1999) 77:2251-2265.

Siebenlist, U. et al., "*E. coli* RNA polymerase interacts homologously with two different promoters," Cell (1980) 20:269-281.

Shaner, N.C. et al., "Improved monomeric red, orange and yellow fluorescent proteins derived from *Discosoma* sp. red fluorescent protein," Nat. Biotechnol. (2004) 22(12):1567-1572.

Sikorski, R.S. and Hieter, P., "A system of shuttle vectors and yeast host strains designed for efficient manipulation of DNA in *Saccharomyces cerevisiae*," Genetics (1989) 122:19-27.

Skolnick, J. et al., "From genes to protein structure and function: novel applications of computational approaches in the genomic era," TIBTECH (2000) 18:34-39.

Smith, G.E. et al., "Modification and secretion of human interleukin 2 produced in insect cells by a baculovirus expression vector," Proc. Natl. Acad. Sci. USA (1985) 82:8404-8408.

Smith et al., "Single-Step Purification of Polypeptides Expressed in *Escherichia coli* as Fusions with Glutathione S-transferase," *Gene* (1988) 67:31-40.

Sorensen, M. et al., "Rapidly maturing red fluorescent protein variants with strongly enhanced brightness in bacteria," FEBS Lett. (2003) 552(2-3):110-114.

Strack, R.L. et al., "A noncytotoxic DsRed variant for whole-cell labeling," Nature Methods (2008) 5(11):955-957.

Suhadolnik et al., "Nucleoside Antibiotics," *J. Bio. Chem.* (1968) 243:12:3532-3537.

Tao, W. et al., "Enhanced green fluorescent protein is a nearly ideal long-term expression tracer for hematopoietic stem cells, whereas DsRed-express fluorescent protein is not," Stem Cells 2007 25(3):670-678.

Terskikh, A. et al., "Fluorescent timer: protein that changes color with time," Science (2000) 290:1585-1588.

Terskikh, A.V. et al., "Analysis of DsRed mutants. Space around the fluorophore accelerates fluorescence development," J. Biol. Chem. (2002) 277(10):7633-7636.

Tilburn, J. et al., "Transformation by integration in *Aspergillus nidulans*," *Gene* (1983) 26:205-221.

Totsune, H. et al., "Chemiluminescence from bamboo shoot cut," Biochem. Biophys. Res. Comm. (1993) 194(3):1025-1029.

Transcription and Translation, a Practical Approach, B.D. Harnes & S.J. Higgins, eds., IRL Press, Oxford-Washington DC (1984) (Book Not Provided/Table of Contents Only).

Tsein, R.Y., "The green fluorescent protein," Annu. Rev. Biochem. (1998) 67:509-544.

Tsein, R.Y., "Rosy dawn for fluorescent proteins," Nat. Biotech. (1999) 17:956-957.

Van Den Berg, J.A. et al., "*Kluyveromyces* as a host for heterologous gene expression: Expression and secretion of prochymosin," Bio/Technology (1990) 8:135-139.

Verkhusha, V.V. et al., "An enhanced mutant of red fluorescent protein DsRed for double labeling and developmental timer of neutral fiber bundle formation," J. Biol. Chem. (2001) 276(32)29621-29624.

Vlak, J.M. et al., "Functional studies on the p10 gene of *Autographa californica* nuclear polyhedrosis virus using a recombinant expressing a p10-β-Galactosidase fusion gene," J. Gen. Virol. (1988) 69:765-776.

Wahlfors, J. et al., "Green Fluorescent Protein (GFP) Fusion Constructs in Gene Therapy Research," Histochem. Cell Biol. (2001) 115:59-65.

Wall, M.A. et al., "The Structural Basis for Red Fluorescence in the Tetrameric GFP Homolog DsRed," Nat. Struct. Biol. (2000) 7:12:1133-1138.

Weiner, M.P. et al., "A Method for the site-directed mono- and multi-mutagenesis of double-stranded DNA," Gene (1993) 126:35-41.

Weiss, S., "Fluorescence Spectroscopy of Single Biomolecules," Science (1999) 283:1676-1683.

Wiehler, J. et al., "Mutants of *Discosoma* Red Fluorescent Protein with a GFP-like C+B158hromophore," FEBS Lett. (2001) 487:384-389.

Wilson, T. and Hastings, J.W., "Bioluminescence," Ann. Rev. Cell Cev. Biol. (1998) 14:197-230.

Witkowski, A. et al., "Conversion of beta-ketoacyl synthase to a malonyl decarboxylase by replacement of the active-site cysteine with glutamine," Biochemistry (1999) 38:11643-11650.

Yang, T-T. et al., "Optimized codon usage and chromophore mutations provide enhanced sensitivity with the green fluorescent protein," Nucleic Acids Research (1996) 24(22):4592-4593.

Yanushevich et al., "A Strategy for the Generation of Non-aggregating Mutants of *Anthozoa* Fluorescent Proteins," *FEBS Lett.* (2002) 511:11-14.

Yarbrough, D. et al., "Refined crystal structure of DsRed, a red fluorescent protein from coral, at 2.0-A resolution," Proc. Natl. Acad. Sci. USA (2001) 98:2:462-467.

Zeng, X. and Hu, J.C., "Detection of Tetramerization Domains in Vivo by Cooperative DNA Binding to Tandem 1 Operator Sites," Gene (1997) 185:245-249.

Zhu, D., "Oligodeoxynucleotide-directed cleavage and repair of a single-stranded vector: A method of site-specific mutagenesis," Anal. Biochem. (1989) 177:120-124.

International Search Report and Written Opinion from International Searching Authority for Application No. PCT/US2005/011753 dated Aug. 4, 2005 (10 pages).

United States Office Action for U.S. Appl. No. 11/100,988 dated Aug. 29, 2006 (7 pages).

United States Office Action for U.S. Appl. No. 10/844,064 dated Jul. 27, 2007 (15 pages).

United States Office Action for U.S. Appl. No. 10/844,064 dated Jul. 8, 2008 (7 pages).

International Search Report from International Searching Authority for Application No. PCT/US02/40539 dated Jul. 28, 2003 (3 pages).

Written Opinion from International Searching Authority for Application No. PCT/US02/40539 dated Jun. 29, 2004 (5 pages).

United States Office Action for U.S. Appl. No. 11/748,641 dated Apr. 16, 2009 (10 pages.

Invitation to Pay Additional Fees and Partial International Search Report for Application No. PCT/US2008/082264 dated Apr. 28, 2009.

United States Office Action for U.S. Appl. No. 10/844,064 dated Jun. 11, 2009 (17 pages).

United States Patent Office Notice of Allowability sent with Notice of Allowance and Fees Due for U.S. Appl. No. 11/748,641 dated Oct. 1, 2009 (4 pages).

MONOMERIC RED FLUORESCENT PROTEINS

CROSS-REFERENCE TO RELATED APPLICATIONS

This application is a continuation of U.S. application Ser. No. 11/100,988, filed Apr. 7, 2005, which claims priority to U.S. Provisional Application No. 60/560,340, filed Apr. 7, 2004, each of which is incorporated by reference in its entirety.

STATEMENT REGARDING FEDERALLY SPONSORED RESEARCH

This invention was made with government support under MCB-9875939, awarded by the National Science Foundation, and under RPG-00-245-01-CSM, awarded by the American Cancer Society. The government has certain rights in the invention.

INTRODUCTION

Fluorescent proteins such as green fluorescent protein (GFP) are invaluable tools used in pure and applied research. Although fluorescent proteins have been widely available for a relatively short time, they have had an important impact on biomedical research, contributing to our understanding of basic cellular and developmental processes that underlie health and disease. GFP and its relatives are widely used for medically-oriented research. For example, GFP has been used to analyze bacterial gene expression during infection, to visualize tumor cell behavior during metastasis, and to monitor GFP fusion proteins in gene therapy studies. Fluorescent proteins are also useful in high-throughput screens for drug discovery.

A red fluorescent protein produced by the coral *Discosoma* and designated DsRed (wild-type DsRed) is potentially useful as a fluorescent reporter protein or as a fusion tag. A red fluorescent protein is particularly attractive because of its suitability for use in conjunction with fluorescent proteins having different fluorescent properties, such as GFP. However, wild-type DsRed suffers from certain drawbacks.

First, the maturation process that yields the red fluorophore is slow, with a half-time of ~12 h at 37° C. Second, wild-type DsRed occurs as a stable tetramer of four very similar polypeptides, which makes its use as a fluorescent reporter in a fusion protein problematic. For example, tetramerization of the DsRed fusion protein may interfere with or perturb the function or localization of the protein. In addition, DsRed tetramers undergo higher-order aggregation. Fusion of DsRed to membrane proteins or to oligomeric proteins often produces large aggregates. Efforts to develop variants of DsRed having a reduced tendency to form tetramers have met with limited success, in that the variants suffer from disadvantages such as undesirable shifts in fluorescence or more rapid photobleaching.

There is, therefore, ongoing interest in developing new fluorescent protein labels with improved characteristics as experimental and clinical tools.

SUMMARY OF THE INVENTION

The present invention provides polynucleotide encoding a variant polypeptide of wild-type DsRed or the rapidly maturing DsRed.T4, a tetrameric variant that has the substitutions described herein below. The variant polypeptide has reduced oligomerization relative wild-type DsRed and has a fluorescence spectra similar to the fluorescence spectra of the wild-type DsRed, the variant polypeptide comprising the amino acid substitutions K83M, K163H, and Y193H and further comprises at least of one amino acid substitutions E26Y, K92T, V96S, T106E, T108Q, I125K, S131A, I180V, and M182K.

In another aspect, the invention provides isolated polynucleotides encoding a variant polypeptide of the rapidly DsRed.T4 and exhibiting reduced oligomerization relative to DsRed.T4 and detectable red fluorescence, the variant polypeptide comprising at least one of amino substitutions K83M or K83L; K163Q, K163M, or K163H; and Y193H, and further comprising at least three amino acid substitutions selected from E26Y, K92T, V96S, T106E, T108Q, I125K, S131A, I180V, and M182K; and further comprising at least three amino acid substitutions selected from the group consisting of R149K, R153Q, H162S, L174T, E176D, Y192N, R216H, H222S, L223G, and F224S.

In other aspects, the invention provides genetic constructs comprising the polynucleotides, vectors comprising the constructs, cells comprising the constructs, variant polypeptides encoded by the polynucleotides, and methods of obtaining expression of the polynucleotides.

DETAILED DESCRIPTION

The present invention provides polypeptide variants of wild-type *Discosoma* sp. red fluorescent protein (DsRed). Wild-type DsRed forms oligomers (e.g., dimers or tetramers) under physiologic conditions, which, in the native polypeptide, appears to play a role in its fluorescence activity. A coding sequence for wild-type *Discosoma* sp. red fluorescent protein (DsRed) is shown in SEQ ID NO:1, and the amino acid sequence of DsRed is shown in SEQ ID NO:2. The polypeptide variants of the present invention have a reduced tendency to oligomerize relative to wild-type DsRed. This reduced tendency to oligomerize may be assessed by any suitable means, whether in vivo or in vitro, as described below.

Polypeptide variants were genetically engineered, as described in detail below, by altering a sequence encoding a rapidly maturing tetrameric variant of wild-type DsRed, designated DsRed.T4 (SEQ ID NO:3). DsRed.T4 is described in further detail in co-pending U.S. patent application Ser. No. 10/844,064, which is incorporated by reference in its entirety. Relative to the wild-type DsRed of SEQ ID NO:2, DsRed.T4 contains the following substitutions:

| | |
|---|---|
| P(-4)L | H41T |
| R2A | N42Q |
| K5E | V44A |
| N6D | A145P |
| T21S | T217A |

Relative to either wild-type DsRed or DsRedT4, the polypeptides of the present invention exhibit a reduced tendency to oligomerize or form tetramers, and exist primarily as monomers under physiologic conditions. The polypeptide variants exhibit detectable red fluorescence. By "detectable red fluorescence" it is meant that the fluorescence overlaps the emission spectra of wild-type DsRed is distinguishable over background. Preferably, the emission spectra is similar to that of wild-type DsRed.

To develop monomeric DsRed variants, a polynucleotide sequence encoding DsRedT4 was modified using the following general approach. As one skilled in the art will appreciate, one could also begin with a polynucleotide encoding another DsRed, for example, wild-type DsRed.

Mutations were introduced into a polynucleotide sequence encoding DsRedT4 to disrupt the tetramerization interfaces that form between DsRed polypeptides. Amino acids suspected of contributing to oligomerization were replaced by amino acids that are likely to reduce oligomerization.

Figure 1:
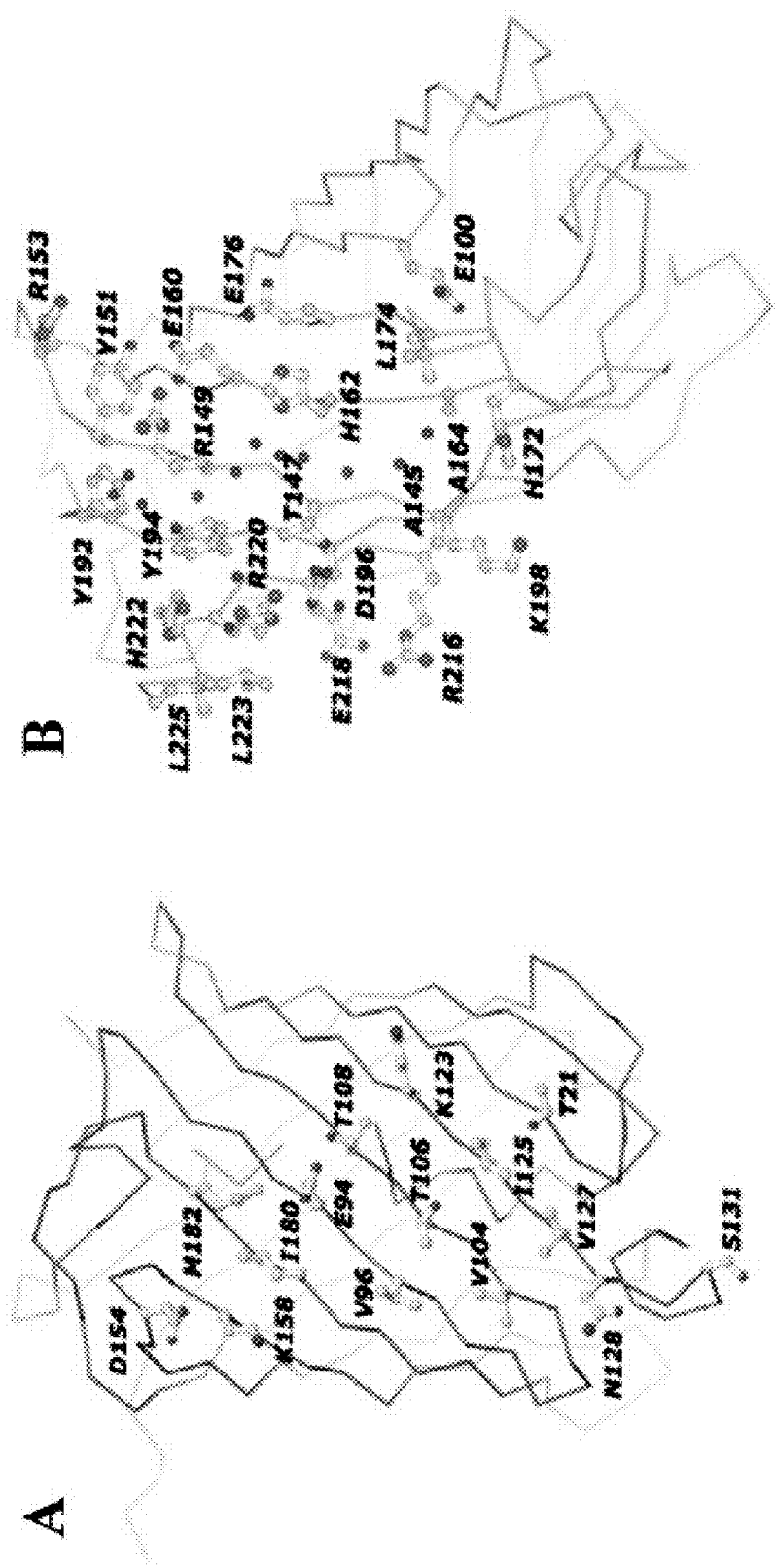
FIG. 1 depicts the hydrophobic interface (FIG. 1A) and the polar interface (1B) involved in tetramerization of DsRed, the latter of which also includes the hydrophobic tail (residues 222-225).

Crystal structures of DsRed reveal residues that may be involved in tetramerization. The region that we have designated the "hydrophobic interface" primarily engages in hydrophobic interactions that exclude the solvent (FIG. 1A). The region that we have designated the "polar interface" primarily engages in polar interactions, although this interface also includes some hydrophobic residues (Leu-174 and the C-terminal tail) that interact with the opposing subunit (FIG. 1B).

Two considerations guided selection of residues to be mutated and the specific substitutions to be tested. First, certain residues are more likely than others to make a significant energetic contribution to oligomerization. For example, a statistical study revealed that isoleucine side chains are often important for protein-protein interactions (Bogan and Thorn, 1998). In designing the variants of the present invention, it was assumed that surface-exposed hydrophobic residues are likely to promote oligomerization, and therefore, such residues were considered prime candidates for mutagenesis. Thus, it is likely that generation of a stable monomer requires modification of residues Ile-180 and Ile-125 (FIG. 1A). Second, the DsRed protein will tolerate substitutions more readily at some positions than at others. Many mutations at the tetramerization interfaces will have secondary effects on the folding and/or maturation of the protein. To make educated guesses about which residues can be mutated and which alternative residues can be substituted, we used sequence alignments between DsRed, GFP, and the other known fluorescent proteins (Matz et al., 1999; Wall et al., 2000).

In some polypeptide variants, mutations in two of the tetramerization interfaces resulted in a loss of tetramerization, which can be measured in vitro or in vivo as described in the Examples, and loss of fluorescence. It was, therefore, speculated that tetramerization may be important for fluorescence in wild-type DsRed, possibly because the autocatalytic formation of the chromophore may stabilize the folded structure of DsRed or because oligomerization may increase the quantum yield.

To restore fluorescence to an oligomerization-disrupted or monomeric DsRed variants, site-directed mutagenesis was performed to introduce specific changes that were expected to stabilize the immature and/or mature forms of the protein. Two general classes of mutations were introduced in an attempt to restore fluorescence after disrupting the tetramer: (1) mutations that may stabilize folding intermediates to permit the protein to mature even in the absence of oligomerization; and (2) mutations expected to rigidify mature DsRed to enhance quantum yield.

In a second strategy to restore fluorescence to an oligomerization-disrupted or monomeric DsRed variant, a wide range of mutations were introduced into either the entire DsRed coding sequence or into a selected segment of the coding sequence. The variants thus generated were screened for improved fluorescence.

The effect of various mutations has, in some cases, been demonstrated, and in other cases, has been presumed or inferred. The mutations can be divided into the following six categories of effects:

1. Mutations that presumably stabilize immature folding intermediates. In tetrameric DsRed variants, K83 and K163 face the interior of the protein. The presence of these highly polar internal residues is likely to destabilize folding intermediates. Therefore, K83M and K163H substitutions were introduced to reduce the polarity at these positions. The K163H substitution is relatively conservative because histidine is still somewhat polar. The K83M substitution introduces a hydrophobic residue, and red-shifts the fluorescence spectra. However, it was discovered by random mutagenesis that a Y193H substitution reverses the spectral changes caused by K83M, and also enhances brightness. Residue 193 is close to residue 83 of the folded protein, so the Y193H substitution may compensate for the reduced polarity caused by K83M. Variants containing the trio of substitutions K83M, K163H, Y193H seem to be stabilized, as indicated by their ability to tolerate interface mutations that are not tolerated by DsRed.T4.

2. Mutations that disrupt the hydrophobic tetramerization interface. This category comprises E26Y, K92T, V96S, T106E, T108Q, I125K, S131A, I180V, and M182K, each of which is predicted to disrupt intersubunit interactions at the hydrophobic interface.

3. Mutations that disrupt the polar tetramerization interface. This category comprises R149K, R153Q, H162S, L174T, E176D, Y192N, R216H, H222S, L223G, F224S, and L225Q, each of which is predicted to disrupt intersubunit interactions at the polar interface. The hydrophobic C-terminal tail of DsRed is considered to be part of the polar interface.

4. Mutations that enhance monomer fluorescence, presumably by stabilizing and/or rigidifying the protein. This category comprises V71A, C117T, V175C, S179T, S203N, and G219A. Note that C117T also eliminates a surface cysteine residue that might otherwise be oxidized within the secretory pathway.

5. Mutations that improve expression in *E. coli*. When a variant such as DsRed.T4 is produced in *E. coli* using its own start codon, the protein levels are much lower than when the same protein is produced using an N-terminal hexahistidine tag, which suggests that the 5' end of the gene is important for expression in bacteria. The coding sequences were altered such that the putative translation products contained substitutions in residues 2-4 and screened for strong expression in *E. coli*. A polypeptide having the substitutions A2D, S3N, and S4T was found to be strongly expressed. These N-terminal mutations probably enhance translation in *E. coli*, an effect that may not occur with expression in eukaryotic cells. In addition, the N-terminal mutations might have some beneficial effect on the maturation and/or stability of DsRed.

6. Mutations that reduce the general "stickiness" of the protein. We introduced a number of surface mutations that lie outside of the tetramerization interfaces that should reduce the tendency of the protein to adhere to other macromolecules. Specifically, we targeted basic residues (especially arginines) and large, hydrophobic residues. The substitutions in this category include R13Q, R36K, K47Q, M141A, and I210V. We have shown that these substitutions do not significantly reduce fluorescence, and expect that variants containing one or more of these substitutions may exhibit reduced aggregation with other macromolecules. Reduced aggregation may be evaluated by comparing the solubility of DsRed variants to that of wild-type DsRed.

An example of a DsRed monomeric variant containing numerous mutations and identified as DsRed.M1 (SEQ ID NO:5) is described below. Of course, useful monomeric variants of the presently claimed invention having fewer mutations than those contained in the DsRed.M1 may be developed using the guidance and teaching herein of this disclosure.

DsRed.M1 was further modified by introducing D6N, a reversion to the native sequence, in order to reduce the number of acidic residues at the N-terminus The additional substitutions K121H, K168E, D169G, D115G, and G116N were made to improve brightness or fluorescence.

Once a DsRed monomeric variant having desirable characteristics is identified, one may, of course, use any polynucleotide sequence encoding the variant to express the variant. For example, the polynucleotide encoding the variant may be modified for optimal expression in a particular organism in view of the preferred codon usage of that organism. The polynucleotide may be operably linked to an inducible or constitutive promoter functional in the intended cell or organism. The polynucleotide may be linked in-fram to a second polynucleotide sequence encoding a polypeptide of interest to form a sequence encoding a fusion protein in which the polypeptide of interest is labeled with the DsRed monomeric variant at its N- or C-terminus.

EXAMPLES

Selection of Amino Acid Substitutions to Reduce Tetramerization

Site-directed mutagenesis using standard methods well-known to one of ordinary skill in the art was used to disrupt the two tetramerization interfaces of DsRed. Various substitutions at each position were made, and fluorescence was evaluated as described below.

The Hydrophobic Interface

Extensive mutagenesis of the hydrophobic interface was performed, beginning with the DsRed.T4 variant. DsRed.T4 contains a T215 substitution. In addition, Met-182, Ile-180, Val-96 and Ile-125 were substituted with more polar residues, and a hydrogen-bonding residue was removed through an S131A substitution. The DsRed.T4 variant having these substitutions was designated DsRed.D1. This variant is probably dimeric. An additional V104A substitution is tolerated in the DsRed.D1 background. It is of note that, in the related fluorescent protein HcRed, a single Leu-to-His mutation in the putative hydrophobic interface at the position corresponding to Ile-125 of DsRed was reportedly sufficient to convert HcRed into a dimer (Gurskaya et al., 2001). Bacterial colonies producing DsRed.D1 are somewhat less fluorescent than those producing DsRed.T4, but the signal with DsRed.D1 is still strong.

The Polar Interface

Initial attempts to mutagenize the polar interface yielded reduced the fluorescence. For example, Leu-174 forms hydrophobic interactions with the opposing subunit, but all of the Leu-174 substitutions that we initially tried, including a conservative change to Val, virtually abolished fluorescence. It was thus concluded that Leu-174 is required for fluorescence and should not be mutated. Similar results were obtained with His-162, which associates with its counterpart on the opposing subunit in an unusual stacking interaction, and with His-222, which inserts into a groove in the opposing subunit. Conservative mutations of these His residues to Ser or Asn severely diminished the fluorescence. Indeed, mutagenesis of most the key residues at the polar interface were found to impair fluorescence.

Assessing Oligomeric State of DsRed Variants

The oligomeric state of a DsRed variant may be assessed by nondenaturing SDS-PAGE or size exclusion chromatography.

For nondenaturing SDS-PAGE, one µg of each purified DsRed variant or wild-type DsRed was mixed with SDS-containing sample buffer on ice and immediately electrophoresed at 4° C. in a 10% polyacrylamide gel, followed by staining with Coomassie Blue. Additional aliquots of wild-type DsRed and DsRed variants were denatured by boiling prior to electrophoresis.

Gel filtration chromatography may be used to indicate whether a fluorescent protein exists predominantly as a monomer, dimer or tetramer (Gurskaya et al., 2001). Optionally, gel filtration will be conducted using the Pharmacia FPLC system. An extension of this method known as small-zone size-exclusion gel filtration chromatography could be used to measure association constants (Raffen and Stevens, 1999).

Oligomerization states and association constants of our DsRed variants may be evaluated using analytical ultracentrifugation (Laue and Stafford, 1999). This approach was used by Baird et al. (2000) for their initial demonstration that DsRed is a tetramer. A Beckman XL-A analytical ultracentrifuge will be used. Velocity sedimentation will be used to ascertain which DsRed species are present (monomers, dimers and/or tetramers), and then equilibrium sedimentation will be used to measure the oligomer association constants (Laue and Stafford, 1999).

Analytical ultracentrifugation will be carried out in collaboration with Borries Demeler (University of Texas Health Sciences Center at San Antonio), who has extensive experience with analytical ultracentrifugation (eg., Demeler and Saber, 1998) and is the author of the state-of-the-art UltraScan II software (www.ultrascan.uthscsa.edu).

An in vivo assay for DsRed oligomerization may be used in a genetic screen. For example, a yeast two-hybrid system such as that reported to have has been used to verify the oligomerization of wild-type DsRed (Baird et al., 2000) may be used to assess the tendency of DsRed variants to oligomerize.

Another approach used to monitor DsRed oligomerization in vivo was to fuse GFP or DsRed to the protein Gos1p in *S. cerevisiae*. Gos1p is a membrane protein anchored to the cytoplasmic face of yeast Golgi cisternae. The GFP-Gos1p fusion protein gives a fluorescence pattern that is typical for the Golgi in *S. cerevisiae*, whereas a wild-type DsRed Gos1p fusion generates large red blobs in the cells, presumably because multiple Golgi cisternae become crosslinked via DsRed tetramerization. Thus, visualizing DsRed-Gos1p fusions provides an in vivo assay for DsRed oligomerization.

In another screening assay, randomly mutagenized DsRed proteins will be fused to the C-terminus of glutathione S-transferase (GST; Smith and Johnson, 1988). Because GST is a dimer (McTigue et al., 1995), the fusion of GST to an oligomeric DsRed variant will generate crosslinked aggregates that will be insoluble upon gentle detergent lysis of the cells. By contrast, the fusion of GST to a monomeric DsRed variant will generate a soluble protein. The concept of using this method to evaluate the oligomeric state of DsRed variants was tested using an expression and detergent lysis protocol similar to that used to evaluate solubility or aggregation of DsRed, fluorescent DsRed.T1, a tetrameric variant, was efficiently extracted from the bacterial cells whereas the fluorescent GST-DsRed.T1 was quantitatively retained in the pellet. It is expected that this assay will provide a sensitive screen for a monomeric DsRed.

Optimizing Spectral Properties

In an earlier stage of this project, we attempted to create a bright, red-shifted DsRed variant. We began with DsRed.T4 and introduced a K83M substitution, which had been shown to red-shift the fluorescence spectra of wild-type DsRed (Baird et al., 2000). In the DsRed.T4 background, K83M red-shifted the spectra (FIG. 2), but substantially reduced the intrinsic brightness of the protein. Screening of randomly mutagenized variants was undertaken to identify variants having restored fluorescence. Surprisingly, an L174Q mutation was found to increase brightness. Subsequent tests confirmed that in the context of K83M, other substitutions at the polar interface, including H162S and H222S, preserve or restore colony fluorescence.

Without being limited as to theory, we speculate that the K83M mutation allows DsRed to tolerate changes at the polar interface by stabilizing the immature form of the DsRed, thereby allowing for correct folding. The cores of most proteins are hydrophobic, but in the case of DsRed, K83 is one of several charged residues that face the interior of the protein (Wall et al., 2000; Yarbrough et al., 2001). It may be that immature DsRed is stabilized by tetramerization, particularly by interactions at the polar interface, and that the K83M substitution renders the immature protein sufficiently stable to fold even in the absence of interactions at the polar interface. Based on this hypothesis, we predict that in the absence of K83M, mutations such as L174Q will decrease the yield of mature DsRed but will not reduce the intrinsic fluorescence of the mature protein. Meanwhile, regardless of the reason, K83M has enabled us to mutagenize the polar interface.

Figure 2:
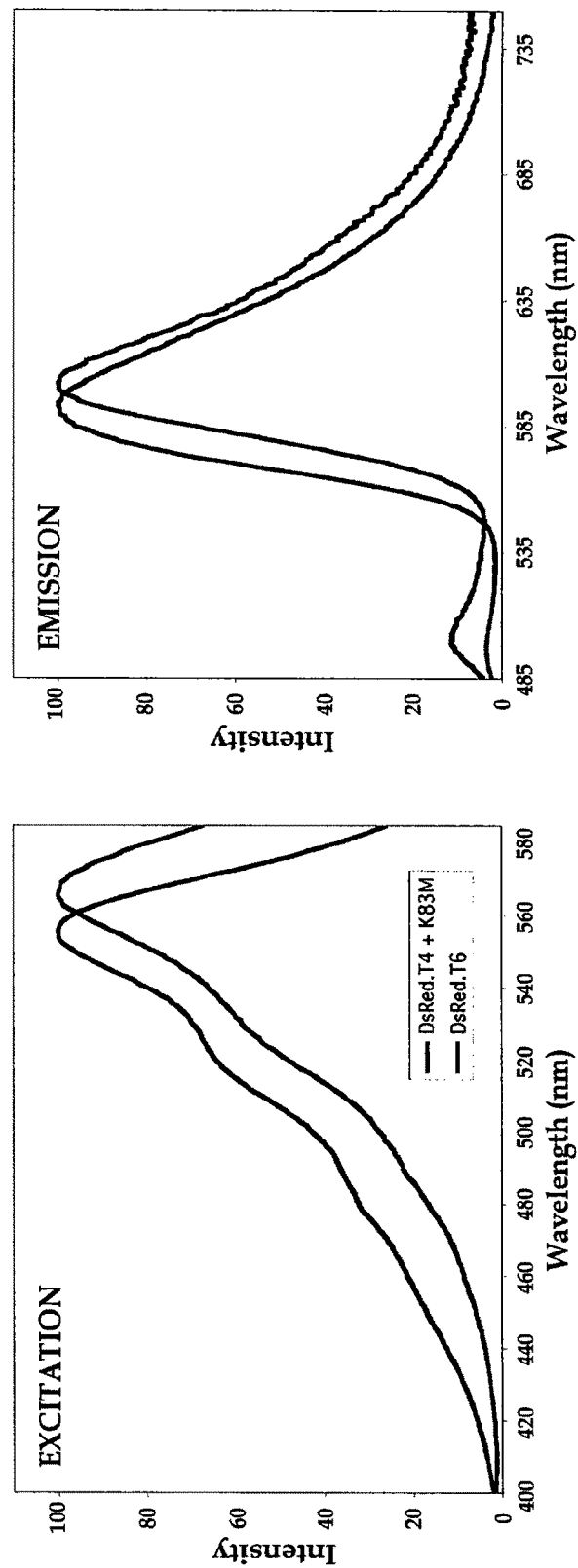
FIG. 2 compares the excitation and emission spectra for a derivative of tetrameric variant DsRed.T4 having a K83M substitution, and a derivative of DsRed.T4 having K83M, K163H, and Y193H substitutions.

To address the reduced fluorescence found with variants having a K83M substitution, two rounds of random mutagenesis and screening were undertaken. Two additional substitutions (K163H and Y193H) that significantly increase the brightness of the purified protein were identified. These new mutations are distinct from L174Q, and they alter residues that face the interior of the protein. The variant of DsRed.T4 having the K83M, K163H, and Y193H substitutions was designated DsRed.T6. As judged by colony fluorescence, DsRed.T6 is comparable to DsRed.T4 in brightness. Interestingly, the spectral red-shifting observed with K83M is largely reversed by the two additional substitutions in DsRed.T6 (FIG. 2). As can be seen from FIG. 2, the K83M substitution red-shifts the excitation and emission peaks by ~20 nm. The two additional substitutions present in DsRed.T6 reverse most of this red-shifting, and also suppress the green emission. We have also introduced K83M, K163H, and Y193H substitutions into the DsRed.D1 background and the resulting variant, designated DsRed.D3, has strong fluorescence and tolerates mutations at the polar interface. We plan is to start with DsRed.D3 and mutate most or all of the residues that contribute to the polar interface.

Preferably, the monomeric DsRed variant of the present invention retains the spectral properties of the tetramer, namely, bright red fluorescence with minimal green emission. However, fluorescent bacterial colonies expressing polypeptides containing substituted amino acids for those of the wild-type DsRed that ordinarily form the hydrophobic tetramerization interface appear somewhat dimmer than colonies of bacteria expressing tetrameric variants. Two kinds of changes may account for decreased fluorescence of the bacterial colonies expressing mutant DsRed. First, a mutation may reduce the intrinsic brightness of DsRed by lowering the extinction coefficient and/or the quantum yield. Second, a mutation might slow DsRed maturation and/or reduce the percentage of the DsRed molecules that eventually become fluorescent. To counteract such effects, random mutagenesis strategy will be used to identify brighter variants of the monomers.

Minimizing the Green Emission of Monomeric DsRed

A predicted side effect of disrupting the DsRed tetramer will be a loss of FRET and a consequent increase in the green emission. To alleviate this problem, mutations that increase the ratio of red to green molecules in mature DsRed may be introduced. Substitutions of K83M, K163H, and Y193H in DsRedT6 correlate with brighter red fluorescence and reduced green emission, relative to that of the DsRed.T4+ K83M variant.

In addition to mutations identified in these random screens, directed mutations aimed at weakening the tetramerization may fortuitously reduce the percentage of green molecules in mature DsRed. For instance, the A145P substitution that we incorporated into DsRed.T3 and DsRed.T4 to lower the green emission was originally generated during our attempts to mutagenize the polar interface. More recently, we found that an H222S substitution at the polar interface decreases the green emission.

Screening for Reduced Blue Excitation

Monomeric variants of interest having significant green emission, may be further mutagenized and screened for reduced green emission or reduced blue excitation. A 488-nm laser is used to excite fluorescence in bacteria containing mutant DsRed proteins, and the bacterial cells are then sorted by flow cytometry to identify clones with reduced green emission. This approach would be more difficult with a monomeric DsRed, because undesirable mutations that caused protein aggregation would suppress the green emission due to FRET. Alternatively, mutants may be screened for reduced blue excitation. When total fluorescence is measured, the signal obtained by excitation with blue light should correlate with the percentage of the DsRed molecules having a green fluorophore, regardless of whether the emission spectrum has been modified by FRET.

The assay for reduced blue excitation is based on our standard slide projector method, except that the plates will be photographed with a digital camera. We will photograph each plate under two conditions. First, the total fluorescence after excitation with blue light will be recorded by illuminating through a 485±11 nm bandpass filter and capturing the emission signal through a Kodak Wratten filter #12, which passes wavelengths above 520 nm (Cronin and Hampton, 1999). The image of the plate will be colorized green using Adobe Photoshop. Second, the total fluorescence after excitation with yellow light will be recorded by illuminating through a 520±20 nm bandpass filter and capturing the emission signal through a Kodak Wratten filter #22, which passes wavelengths above 550 nm. This image of the plate will be colorized red. The red image will be due almost exclusively to DsRed molecules with the red fluorophore, whereas the green image will include a strong contribution from DsRed molecules with the green fluorophore. Upon merger of the red and green images, most of the colonies will appear yellow, but colonies having an increased ratio of red to green molecules will appear orange.

Evaluating Solubilities

One approach to evaluating solubilities of the fluorescent proteins in is as follows. $E.\ coli$ cells carrying inducible expression vectors encoding hexahistidine-tagged wild-type DsRed or DsRed variants were grown to an optical density (OD) ($\lambda$=600 nm) of 0.5, induced for 7 h, lysed with B-PER II detergent (Pierce) and centrifuged for 20 min at 27,000×g. Equivalent amounts of the pellet and supernatant fractions were subjected to SDS PAGE followed by immunoblotting with an anti-hexahistidine antibody. The percentage of each protein in the supernatant fraction was then quantified for each protein and the percentage of protein molecules extracted (i.e., solubilized) was determined. Typically, only about 25% of the wild-type DsRed molecules are solubilized. Suitably, at least 30% of DsRed variant molecules are solubilized. Preferably, at least 50% of DsRed variant molecules are solubilized. More preferably, at least 70% of DsRed variant molecules are solubilized.

Another approach to evaluate variants for reduced aggregation is by nondenaturing SDS-PAGE. One μg of each purified DsRed variant was mixed with SDS-containing sample buffer on ice and immediately electrophoresed at 4° C. in a 10% polyacrylamide gel, followed by staining with Coomassie Blue. Additional aliquots of wild-type DsRed and DsRed variants were denatured by boiling prior to electrophoresis. Migration of proteins as a diffuse band that may reflect the formation of higher-order oligomers, whereas formation of a sharp band or bands of the appropriate size suggests reduce aggregation.

Creation and Characterization of a Red Fluorescent DsRed Monomer

A coding sequence and the amino acid sequence of one mutant according to the present invention, designated DsRed.M1, is shown as SEQ ID NO:4 and SEQ ID NO: 5, respectively. DsRed.M1 contains the following 37 substitutions relative to DsRed.T4:

| | | | |
|---|---|---|---|
| A2D* | V96S | K163H | I210V |
| S3N | T106E | L174T | R216H |
| S4T | T108Q | V175C | G219A |
| R13Q | C117T | E176D | H222S |
| E26Y | I125K | S179T | L223G |
| R36K | S131A | I180V | F224S |
| K47Q | M141A | M182K | L225Q |
| V71A | R149K | Y192N | |
| K83M | R153Q | Y193H | |
| K92T | H162S | S203N | |

*A2D is a second mutation of residue 2, which was an arginine in wild-type DsRed.

Oligomeric State: DsRed.M1 behaves functionally as a monomer. The protein appears to be monomeric as judged by nondenaturing SDS-PAGE or size exclusion chromatography.

Brightness: The DsRed.M1 mature protein exhibits detectable red fluorescence, but is less bright than tetrameric variants, such as DsRed.T4. DsRed.M1 is also less bright than a monomeric red fluorescent DsRed protein designated mRFP1, which was generated by Tsien et al. (US 2003/0170911 A1)

Spectral Properties: In contrast to mRFP1, which has a red-shift, DsRed.M1 has excitation and emission spectra similar to those of the tetrameric DsRed variants. Surprisingly, DsRed.M1 has negligible green emission. The lack of green emission is fortunate, and rather unexpected, given that the tetrameric DsRed variants exhibit green emission that is largely suppressed by intersubunit resonance energy transfer.

Photostability: mRFP 1 photobleaches much faster than the tetrameric DsRed variants, an effect that may correlate with the altered spectral properties of mRFP1. It is expected that DsRed.M1 will be more photostable than mRFP1 because the spectral properties of DsRed.M1 are similar to those of the tetrameric variants.

Maturation: DsRed.M1 appears to retain the rapid maturation of the parental DsRed.T4, which is considerably faster than that wild-type of DsRed.

Each publication cited in herein or in the appendix is incorporated by reference in its entirety. Also incorporated by reference in its entirety is WO 03/054158A2.

LITERATURE CITED

Baird, G. S., D. A. Zacharias, and R. Y. Tsien. 2000. Biochemistry, mutagenesis, and oligomerization of DsRed, a red fluorescent protein from coral. Proc. Natl. Acad. Sci. USA. 97:11984-11989.

Bogan, A. A., and K. S. Thorn. 1998. Anatomy of hot spots in protein interfaces. J. Mol. Biol. 280:1-9.

Cronin, S., and R. Hampton. 1999. A genetics-friendly GFP assay. Trends Cell Biol. 9:36.

Demeler, B., and H. Saber. 1998. Determination of molecular parameters by fitting sedimentation data to finite-element solutions of the Lamm equation. Biophys. J. 74:444-454.

Gurskaya, N. G., A. F. Fradkov, A. Terskikh, M. V. Matz, Y. A. Labas, V. I. Martynov, Y. G. Yanushevich, K. A. Lukyanov, and S. A. Lukyanov. 2001. GFP-like chromoproteins as a source of far-red fluorescent proteins. FEBS Lett. 507:16-20.

Laue, T. M., and W.F. Stafford, 3rd. 1999. Modern applications of analytical ultracentrifugation. Annu. Rev. Biophys. Biomol. Struct. 28:75-100.

Matz, M. V., A. F. Fradkov, Y. A. Labas, A. P. Savitsky, A. G. Zaraisky, M. L. Markelov, and S. A. Lukyanov. 1999. Fluorescent proteins from nonbioluminescent *Anthozoa* species. Nat. Biotechnol. 17:969-973.

McTigue, M. A., D. R. Williams, and J. A. Tainer. 1995. Crystal structures of a schistosomal drug and vaccine target: glutathione S-transferase from *Schistosoma japonica* and its complex with the leading antischistosomal drug praziquantel. J. Mol. Biol. 246:21-27.

Pierce, D. W., and R. D. Vale. 1999. Single-molecule fluorescence detection of green fluorescence protein and application to single-protein dynamics. In Green Fluorescent Proteins (Methods in Cell Biology, Vol. 58). K. F. Sullivan, and S. A. Kay, editors. Academic Press, San Diego. 49-73.

Raffen, R., and F. J. Stevens. 1999. Small zone, high-speed gel filtration chromatography to detect protein aggregation associated with light chain pathologies. Methods Enzymol. 309:318-332.

Smith, D. B., and K. S. Johnson. 1988. Single-step purification of polypeptides expressed in *Escherichia coli* as fusions with glutathione S-transferase. Gene. 67:31-40.

Tsien, R. Y. 1998. The green fluorescent protein. Annu. Rev. Biochem. 67:509-544.

Wall, M. A., M. Socolich, and R. Ranganathan. 2000. The structural basis for red fluorescence in the tetrameric GFP homolog DsRed. Nat. Struct. Biol. 7:1133-1138.

Yarbrough, D., R. M. Wachter, K. Kallio, M. V. Matz, and S. J. Remington. 2001. Refined crystal structure of DsRed, a red fluorescent protein from coral, at 2.0-Å resolution. Proc. Natl. Acad. Sci. USA. 98:462-467.

We claim:

1. An isolated polynucleotide encoding a variant polypeptide of the rapidly maturing Discosoma red fluorescent protein T4 (DsRed.T4) consisting of SEQ ID NO:3, wherein the variant polypeptide has reduced oligomerization relative to wild-type DsRed, and matures more rapidly than wild-type DsRed, and wherein the variant polypeptide comprises substitutions: (A) at least one amino acid substitution selected from the group consisting of K83M, K83L, K163Q, K163M, K163H, and Y193H, (B) at least three amino acid substitutions selected from the group consisting of E26Y, K92T, V96S, T106E, T108Q, I125K, S131A, I180V, and M182K, (C) at least three amino acid substitutions selected from the group consisting of R149K, R153Q, H162S, L174T, E176D, Y192N, R216H, H222S, L223G, and F224S, and (D) at least one amino acid substitution selected from the group consisting of V71A, C117T, S175C, S179T, S203N, and G219A.

2. A variant polypeptide of DsRed.T4 consisting of SEQ ID NO:3 wherein the variant polypeptide has reduced oligomerization relative to wild-type DsRed and matures more rapidly than wild-type DsRed, and wherein the variant polypeptide comprises substitutions: (A) at least one amino acid substitution selected from the group consisting of K83M, K83L, K163Q, K163M, K163H, and Y193H, (B) at least three amino acid substitutions selected from the group consisting of E26Y, K92T, V96S, T106E, T108Q, I125K, S131A, I180V, and M182K, and (C) at least three amino acid substitutions selected from the group consisting of R149K, R153Q, H162S, L174T, E176D, Y192N, R216H, H222S, L223G, and F224S.

3. A polynucleotide encoding a fusion protein comprising the variant polypeptide of claim 2.

4. A fusion protein comprising the variant polypeptide of claim 2.

* * * * *

SEQUENCE LISTING

<160> NUMBER OF SEQ ID NOS: 5

<210> SEQ ID NO 1
<211> LENGTH: 678
<212> TYPE: DNA
<213> ORGANISM: Unknown
<220> FEATURE:
<223> OTHER INFORMATION: wild-type red fluorescent protein based on
      Discosoma species

<400> SEQUENCE: 1

```
atgaggtctt ccaagaatgt tatcaaggag ttcatgaggt ttaaggttcg catggaagga      60
acggtcaatg ggcacgagtt tgaaatagaa ggcgaaggag aggggaggcc atacgaaggc     120
cacaataccg taaagcttaa ggtaaccaag ggggaccctt tgccatttgc ttgggatatt     180
ttgtcaccac aatttcagta tggaagcaag gtatatgtca agcaccctgc cgacatacca     240
gactataaaa agctgtcatt tcctgaagga tttaatggg aaagggtcat gaactttgaa     300
gacggtggcg tcgttactgt aacccaggat ccagtttgc aggatggctg tttcatctac     360
aaggtcaagt tcattggcgt gaactttcct tccgatggac ctgttatgca aagaagaca     420 atgggctggg aagccagcac tgagcgtttg tatcctcgtg atggcgtgtt gaaggagag     480 attcataagg ctctgaagct gaaagacggt ggtcattacc tagttgaatt caaaagtatt     540
tacatggcaa agaagcctgt gcagctacca gggtactact atgttgactc caaactggat     600
ataacaagcc acaacgaaga ctatacaatc gttgagcagt atgaaagaac cgagggacgc     660
caccatctgt tcctttaa                                                  678
```

<210> SEQ ID NO 2
<211> LENGTH: 225
<212> TYPE: PRT
<213> ORGANISM: Unknown
<220> FEATURE:
<223> OTHER INFORMATION: wild-type red fluorescent protein based on
      Discosoma species

<400> SEQUENCE: 2

```
Met Arg Ser Ser Lys Asn Val Ile Lys Glu Phe Met Arg Phe Lys Val
1               5                   10                  15

Arg Met Glu Gly Thr Val Asn Gly His Glu Phe Glu Ile Glu Gly Glu
            20                  25                  30

Gly Glu Gly Arg Pro Tyr Glu Gly His Asn Thr Val Lys Leu Lys Val
        35                  40                  45

Thr Lys Gly Gly Pro Leu Pro Phe Ala Trp Asp Ile Leu Ser Pro Gln
    50                  55                  60

Phe Gln Tyr Gly Ser Lys Val Tyr Val Lys His Pro Ala Asp Ile Pro
65                  70                  75                  80

Asp Tyr Lys Lys Leu Ser Phe Pro Glu Gly Phe Lys Trp Glu Arg Val
                85                  90                  95

Met Asn Phe Glu Asp Gly Gly Val Val Thr Val Thr Gln Asp Ser Ser
            100                 105                 110

Leu Gln Asp Gly Cys Phe Ile Tyr Lys Val Lys Phe Ile Gly Val Asn
        115                 120                 125

Phe Pro Ser Asp Gly Pro Val Met Gln Lys Lys Thr Met Gly Trp Glu
    130                 135                 140

Ala Ser Thr Glu Arg Leu Tyr Pro Arg Asp Gly Val Leu Lys Gly Glu
145                 150                 155                 160
```

Ile His Lys Ala Leu Lys Leu Lys Asp Gly Gly His Tyr Leu Val Glu
                165                 170                 175

Phe Lys Ser Ile Tyr Met Ala Lys Lys Pro Val Gln Leu Pro Gly Tyr
            180                 185                 190

Tyr Tyr Val Asp Ser Lys Leu Asp Ile Thr Ser His Asn Glu Asp Tyr
        195                 200                 205

Thr Ile Val Glu Gln Tyr Glu Arg Thr Glu Gly Arg His His Leu Phe
    210                 215                 220

Leu
225

<210> SEQ ID NO 3
<211> LENGTH: 225
<212> TYPE: PRT
<213> ORGANISM: Unknown
<220> FEATURE:
<223> OTHER INFORMATION: rapidly maturing DsRed.T4 red fluorescent
      protein based on Discosoma species

<400> SEQUENCE: 3

Met Ala Ser Ser Glu Asp Val Ile Lys Glu Phe Met Arg Phe Lys Val
1               5                   10                  15

Arg Met Glu Gly Ser Val Asn Gly His Glu Phe Glu Ile Glu Gly Glu
            20                  25                  30

Gly Glu Gly Arg Pro Tyr Glu Gly Thr Gln Thr Ala Lys Leu Lys Val
        35                  40                  45

Thr Lys Gly Gly Pro Leu Pro Phe Ala Trp Asp Ile Leu Ser Pro Gln
    50                  55                  60

Phe Gln Tyr Gly Ser Lys Val Tyr Val Lys His Pro Ala Asp Ile Pro
65                  70                  75                  80

Asp Tyr Lys Lys Leu Ser Phe Pro Glu Gly Phe Lys Trp Glu Arg Val
                85                  90                  95

Met Asn Phe Glu Asp Gly Gly Val Val Thr Val Thr Gln Asp Ser Ser
            100                 105                 110

Leu Gln Asp Gly Cys Phe Ile Tyr Lys Val Lys Phe Ile Gly Val Asn
        115                 120                 125

Phe Pro Ser Asp Gly Pro Val Met Gln Lys Lys Thr Met Gly Trp Glu
    130                 135                 140

Pro Ser Thr Glu Arg Leu Tyr Pro Arg Asp Gly Val Leu Lys Gly Glu
145                 150                 155                 160

Ile His Lys Ala Leu Lys Leu Lys Asp Gly Gly His Tyr Leu Val Glu
                165                 170                 175

Phe Lys Ser Ile Tyr Met Ala Lys Lys Pro Val Gln Leu Pro Gly Tyr
            180                 185                 190

Tyr Tyr Val Asp Ser Lys Leu Asp Ile Thr Ser His Asn Glu Asp Tyr
        195                 200                 205

Thr Ile Val Glu Gln Tyr Glu Arg Ala Glu Gly Arg His His Leu Phe
    210                 215                 220

Leu
225

<210> SEQ ID NO 4
<211> LENGTH: 678
<212> TYPE: DNA
<213> ORGANISM: Unknown
<220> FEATURE:
<223> OTHER INFORMATION: mutant red fluorescent protein DsRed.M1 based
      on Discosoma species
<220> FEATURE:

<221> NAME/KEY: CDS
<222> LOCATION: (1)..(678)

<400> SEQUENCE: 4

| | | | | | | | | | | | | | | | | |
|---|---|---|---|---|---|---|---|---|---|---|---|---|---|---|---|---|
| atg | gac | aac | acc | gag | gac | gtc | atc | aag | gag | ttc | atg | cag | ttc | aag | gtg | 48 |
| Met | Asp | Asn | Thr | Glu | Asp | Val | Ile | Lys | Glu | Phe | Met | Gln | Phe | Lys | Val | |
| 1 | | | | 5 | | | | | 10 | | | | | 15 | | |
| cgc | atg | gag | ggc | tcc | gtg | aac | ggc | cac | tac | ttc | gag | atc | gag | ggc | gag | 96 |
| Arg | Met | Glu | Gly | Ser | Val | Asn | Gly | His | Tyr | Phe | Glu | Ile | Glu | Gly | Glu | |
| | | | 20 | | | | | 25 | | | | | 30 | | | |
| ggc | gag | ggc | aag | ccc | tac | gag | ggc | acc | cag | acc | gcc | aag | ctg | cag | gtg | 144 |
| Gly | Glu | Gly | Lys | Pro | Tyr | Glu | Gly | Thr | Gln | Thr | Ala | Lys | Leu | Gln | Val | |
| | 35 | | | | | 40 | | | | | 45 | | | | | |
| acc | aag | ggc | ggc | ccc | ctg | ccc | ttc | gcc | tgg | gac | atc | ctg | tcc | ccc | cag | 192 |
| Thr | Lys | Gly | Gly | Pro | Leu | Pro | Phe | Ala | Trp | Asp | Ile | Leu | Ser | Pro | Gln | |
| 50 | | | | | 55 | | | | | 60 | | | | | | |
| ttc | cag | tac | ggc | tcc | aag | gcc | tac | gtg | aag | cac | ccc | gcc | gac | atc | ccc | 240 |
| Phe | Gln | Tyr | Gly | Ser | Lys | Ala | Tyr | Val | Lys | His | Pro | Ala | Asp | Ile | Pro | |
| 65 | | | | | 70 | | | | | 75 | | | | | 80 | |
| gac | tac | atg | aag | ctg | tcc | ttc | ccc | gag | ggc | ttc | acc | tgg | gag | cgc | tcc | 288 |
| Asp | Tyr | Met | Lys | Leu | Ser | Phe | Pro | Glu | Gly | Phe | Thr | Trp | Glu | Arg | Ser | |
| | | | | 85 | | | | | 90 | | | | | 95 | | |
| atg | aac | ttc | gag | gac | ggc | ggc | gtg | gtg | gag | gtg | cag | cag | gac | tcc | tcc | 336 |
| Met | Asn | Phe | Glu | Asp | Gly | Gly | Val | Val | Glu | Val | Gln | Gln | Asp | Ser | Ser | |
| | | | 100 | | | | | 105 | | | | | 110 | | | |
| ctg | cag | gac | ggc | acc | ttc | atc | tac | aag | gtg | aag | ttc | aag | ggc | gtg | aac | 384 |
| Leu | Gln | Asp | Gly | Thr | Phe | Ile | Tyr | Lys | Val | Lys | Phe | Lys | Gly | Val | Asn | |
| | | 115 | | | | | 120 | | | | | 125 | | | | |
| ttc | ccc | gcc | gac | ggc | ccc | gta | atg | cag | aag | aag | act | gcc | ggc | tgg | gag | 432 |
| Phe | Pro | Ala | Asp | Gly | Pro | Val | Met | Gln | Lys | Lys | Thr | Ala | Gly | Trp | Glu | |
| | 130 | | | | | 135 | | | | | 140 | | | | | |
| ccc | tcc | acc | gag | aag | ctg | tac | ccc | cag | gac | ggc | gtg | ctg | aag | ggc | gag | 480 |
| Pro | Ser | Thr | Glu | Lys | Leu | Tyr | Pro | Gln | Asp | Gly | Val | Leu | Lys | Gly | Glu | |
| 145 | | | | | 150 | | | | | 155 | | | | | 160 | |
| atc | tcc | cac | gcc | ctg | aag | ctg | aag | gac | ggc | ggc | cac | tac | acc | tgc | gac | 528 |
| Ile | Ser | His | Ala | Leu | Lys | Leu | Lys | Asp | Gly | Gly | His | Tyr | Thr | Cys | Asp | |
| | | | | 165 | | | | | 170 | | | | | 175 | | |
| ttc | aag | acc | gtg | tac | aag | gcc | aag | aag | ccc | gtg | cag | ctg | ccc | ggc | aac | 576 |
| Phe | Lys | Thr | Val | Tyr | Lys | Ala | Lys | Lys | Pro | Val | Gln | Leu | Pro | Gly | Asn | |
| | | | 180 | | | | | 185 | | | | | 190 | | | |
| cac | tac | gtg | gac | tcc | aag | ctg | gac | atc | acc | aac | cac | aac | gag | gac | tac | 624 |
| His | Tyr | Val | Asp | Ser | Lys | Leu | Asp | Ile | Thr | Asn | His | Asn | Glu | Asp | Tyr | |
| | | 195 | | | | | 200 | | | | | 205 | | | | |
| acc | gtg | gtg | gag | cag | tac | gag | cac | gcc | gag | gcc | cgc | cac | tcc | ggc | tcc | 672 |
| Thr | Val | Val | Glu | Gln | Tyr | Glu | His | Ala | Glu | Ala | Arg | His | Ser | Gly | Ser | |
| | 210 | | | | | 215 | | | | | 220 | | | | | |
| cag | tag | | | | | | | | | | | | | | | 678 |
| Gln | | | | | | | | | | | | | | | | |
| 225 | | | | | | | | | | | | | | | | |

<210> SEQ ID NO 5
<211> LENGTH: 225
<212> TYPE: PRT
<213> ORGANISM: Unknown
<220> FEATURE:
<223> OTHER INFORMATION: Synthetic Construct

<400> SEQUENCE: 5

Met Asp Asn Thr Glu Asp Val Ile Lys Glu Phe Met Gln Phe Lys Val
1               5                   10                  15

Arg Met Glu Gly Ser Val Asn Gly His Tyr Phe Glu Ile Glu Gly Glu
            20                  25                  30

```
Gly Glu Gly Lys Pro Tyr Glu Gly Thr Gln Thr Ala Lys Leu Gln Val
        35                  40              45

Thr Lys Gly Gly Pro Leu Pro Phe Ala Trp Asp Ile Leu Ser Pro Gln
    50              55                  60

Phe Gln Tyr Gly Ser Lys Ala Tyr Val Lys His Pro Ala Asp Ile Pro
65              70                  75                      80

Asp Tyr Met Lys Leu Ser Phe Pro Glu Gly Phe Thr Trp Glu Arg Ser
            85                      90                  95

Met Asn Phe Glu Asp Gly Gly Val Val Glu Val Gln Gln Asp Ser Ser
            100             105             110

Leu Gln Asp Gly Thr Phe Ile Tyr Lys Val Lys Phe Lys Gly Val Asn
        115                 120             125

Phe Pro Ala Asp Gly Pro Val Met Gln Lys Lys Thr Ala Gly Trp Glu
        130             135             140

Pro Ser Thr Glu Lys Leu Tyr Pro Gln Asp Gly Val Leu Lys Gly Glu
145             150             155                         160

Ile Ser His Ala Leu Lys Leu Lys Asp Gly Gly His Tyr Thr Cys Asp
            165             170             175

Phe Lys Thr Val Tyr Lys Ala Lys Lys Pro Val Gln Leu Pro Gly Asn
            180             185             190

His Tyr Val Asp Ser Lys Leu Asp Ile Thr Asn His Asn Glu Asp Tyr
        195             200             205

Thr Val Val Glu Gln Tyr Glu His Ala Glu Ala Arg His Ser Gly Ser
    210             215             220

Gln
225
```